United States Patent [19]
Ansite

[11] Patent Number: 4,622,963
[45] Date of Patent: Nov. 18, 1986

[54] SELF-CONTAINED PORTABLE SINGLE PATIENT VENTILATOR/RESUSCITATOR

[75] Inventor: William K. Ansite, Glendale, Calif.

[73] Assignee: Figgie International Inc., Willoughby, Ohio

[21] Appl. No.: 722,440

[22] Filed: Apr. 15, 1985

Related U.S. Application Data

[63] Continuation of Ser. No. 459,405, Jan. 20, 1983, abandoned.

[51] Int. Cl.$^4$ ............................................. A61M 16/00
[52] U.S. Cl. ........................... 128/203.27; 128/204.17
[58] Field of Search ...................... 128/201.25, 204.21, 128/204.23, 204.24, 204.25, 204.26, 205.11, 205.12, 202.26, 205.13, 205.14, 205.15, 205.16, 205.17

[56] References Cited

U.S. PATENT DOCUMENTS

| | | | |
|---|---|---|---|
| Re. 23,845 | 6/1954 | Seeler | 128/204.25 |
| 2,106,393 | 1/1938 | Hausmann | 128/202.26 |
| 2,123,334 | 7/1938 | Hausmann | 128/173 |
| 2,444,029 | 7/1946 | Bowen | 128/142 |
| 2,507,450 | 5/1950 | Millikan et al. | 128/202.26 |
| 2,897,833 | 8/1959 | Seeler | 128/205.11 |
| 3,191,596 | 6/1965 | Bird et al. | 128/204.25 |
| 3,292,617 | 12/1966 | McDonough | 128/205.15 |
| 3,441,020 | 4/1969 | Wortz et al. | 128/207.11 |
| 3,536,070 | 10/1970 | Bovard | 128/142.3 |
| 3,733,008 | 5/1973 | Churchill et al. | 222/6 |
| 3,773,044 | 11/1973 | Wallace | 128/142.6 |
| 3,815,592 | 6/1974 | Staub, Jr. | 128/142 |
| 3,817,246 | 6/1974 | Weigl | 128/204.24 |
| 3,868,225 | 2/1975 | Tidd | 128/202.26 |
| 3,901,230 | 8/1975 | Henkin | 128/205.17 |
| 3,913,576 | 10/1975 | Martin et al. | 128/204.25 |
| 3,915,164 | 10/1975 | Bird | 128/204.25 |
| 3,916,888 | 11/1975 | Buck et al. | 128/204.21 |
| 3,938,512 | 2/1976 | Mausteller et al. | 128/191 R |
| 4,057,059 | 11/1977 | Reid, Jr. et al. | 128/204.24 |
| 4,060,078 | 11/1977 | Bird | 128/204.25 |
| 4,098,271 | 7/1978 | Maddock | 128/205.25 |
| 4,108,171 | 8/1978 | Nyman et al. | 128/204.26 |
| 4,120,300 | 10/1978 | Tiep | 128/205.13 |
| 4,127,123 | 11/1978 | Bird | 128/204.25 |
| 4,292,967 | 10/1981 | Pasternack | 128/202.26 |

OTHER PUBLICATIONS

"pneuPAC" Ventilator/Resuscitator by Bear Medical Systems, Inc. the Bear 2 Ventilator by Bear Medical Systems, Inc.
2nd Ed. of "Respiratory Therapy Equipment" by Steven P. McPherson, publ. 1981 by The C. V. Mosby Company particularly pp. 234 to 237.
The Scott "SCRAM" Emergency Escape Breathing Device, U.S. patent application Ser. No. 217,881 filed Dec. 15, 1980.
Dynamco Logic Components—Bulletin 300, C. A. Norgren Co.—fluidic components.

Primary Examiner—Henry J. Recla
Attorney, Agent, or Firm—Christel, Bean & Linihan

[57] ABSTRACT

A single patient ventilator/resuscitator of the type which has a timed cycle of operation, but which a patient can override in response to his physiological needs. The ventilator/resuscitator has a source of oxygen, for example a chlorate candle (26), the oxygen source being associated with a filter (32) capable of filtering toxic or harmful contaminants from the atmosphere. Fluid operated delivery and control means are associated with the oxygen source and includes an air oxygen delivery means (20) shiftable between inspiratory and expiratory modes. When the delivery means is in the inspiratory mode at least a portion of the oxygen output is delivered to the patient (14), and when the delivery means is in the expiratory mode at least a portion of the oxygen output is delivered to an accumulator (54). The fluid operated control means (24) will cause the delivery means to cycle between its inspiratory and expiratory positions in a timed cycle established by timing modules (88, 89). The control means additionally includes pressure sensing devices (90, 92) which are capable of causing the control means (24) to shift the delivery means to an inspiratory mode when the patient initiates an inspiratory effort, and which are also capable of switching the delivery means to an expiratory mode when the pressure to the patient exceeds its set peak pressure.

12 Claims, 2 Drawing Figures

Fig. 2.

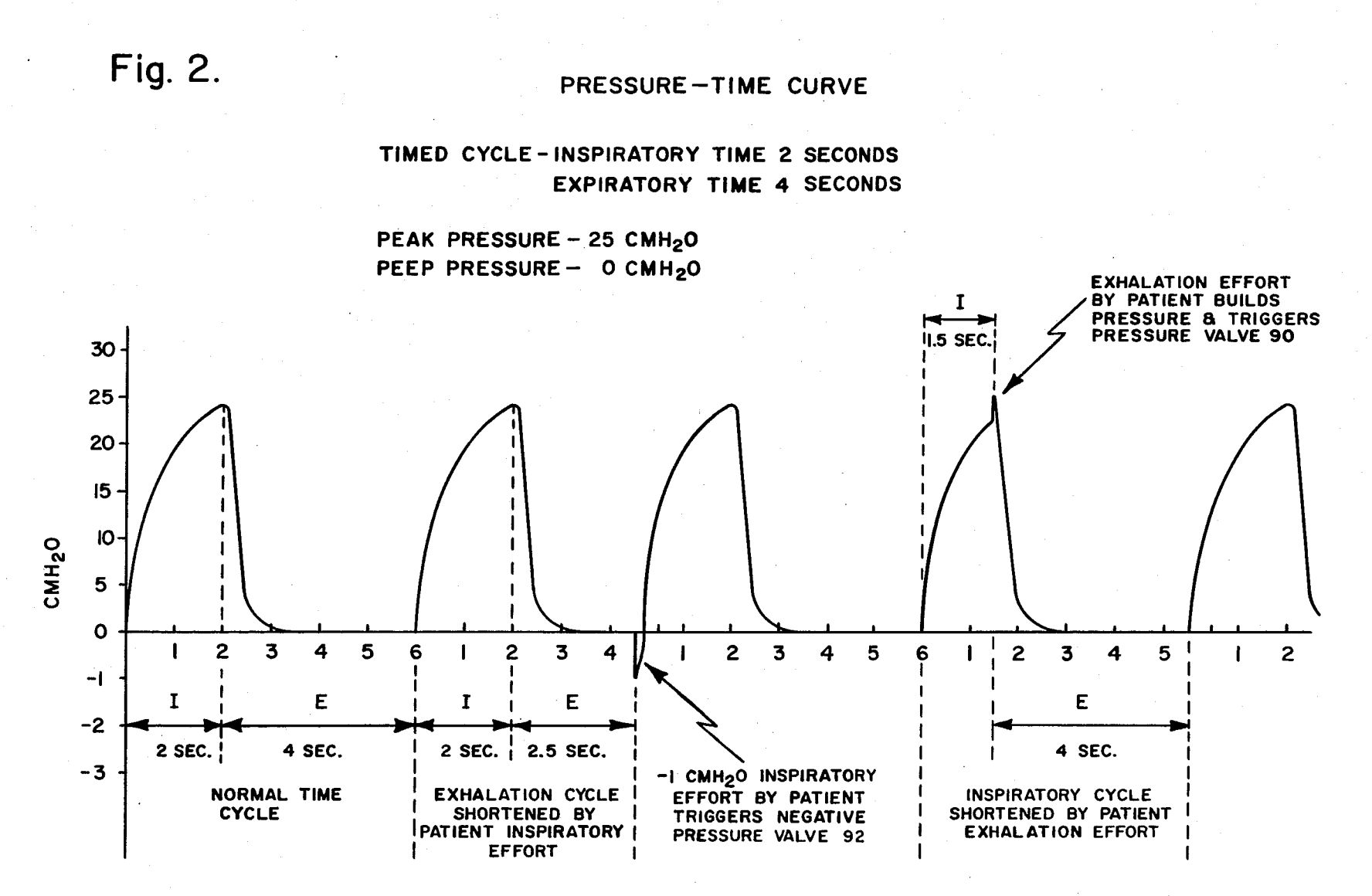

PRESSURE-TIME CURVE

TIMED CYCLE-INSPIRATORY TIME 2 SECONDS
EXPIRATORY TIME 4 SECONDS

PEAK PRESSURE - 25 $CMH_2O$
PEEP PRESSURE - 0 $CMH_2O$

4,622,963

SELF-CONTAINED PORTABLE SINGLE PATIENT VENTILATOR/RESUSCITATOR

This application is a continuation of application Ser. No. 06/459,405, filed 1/20/83 now abandoned.

FIELD OF THE INVENTION

The present invention relates generally to respiratory apparatus, and more particularly to a self-contained portable respiratory device which can be used with a single patient either as a ventilator or as a resuscitator for a limited period of time.

BACKGROUND OF THE INVENTION

Various types of respiratory devices are well-known in the art, and the present invention deals with that class of devices generally referred to as either resuscitators and/or ventilators, depending upon their primary intended usage. As used in this application, a resuscitator is defined as an apparatus utilized for initiating respiration in a person whose breathing has stopped. Similarly, a ventilator is defined as a positive pressure apparatus, other than a resuscitator, utilized to assist in pulmonary ventilation. Most types of known prior art have been developed for use in hospitals and are adapted to be powered by electrical current received from the hospital, and are also adapted to utilize the hospital oxygen supply system.

While some portable resuscitators have been known in the past, these devices typically used bottled oxygen, which has an adverse oxygen supply to weight ratio. In addition, devices which rely on bottled oxygen typically have a relatively short shelf life when compared to devices which rely on chemical oxygen generators.

Known portable resuscitators have operated only in a timed cycle mode wherein a volume of an air/oxygen mixture is forced into a patient's lungs for a period of time and then the air/oxygen mixture is permitted to expire for another period of time, the periods of time being selected to approximate a normal breathing cycle. Known portable ventilators have operated only in a demand cycle wherein each inspiratory phase of ventilation is triggered by the inspiratory effect of the patient's breathing. Demand mode ventilators are not suitable for use as resuscitators, as the patient is incapable of triggering their operation. Similarly, timed cycle resuscitators are not desirable for use as ventilators or with patients who start breathing on their own, as a mismatch of the breathing cycle to the physiological needs of the patient could be traumatic.

OBJECTS AND SUMMARY OF THE INVENTION

It is an object of the present invention to provide a self-contained portable ventilator/resuscitator which overcomes the disadvantages of the known prior art devices. Therefore, it is an object to provide a self-contained portable single patient ventilator/resuscitator having an acceptable oxygen supply to weight ratio, a relatively long shelf life, and which can operate either as a ventilator or a resuscitator, such a portable unit normally being operated in a timed cycle mode, the timed cycle capable of being overridden by a patient's inspiratory or expiratory efforts.

More specifically, it is an object of the present invention to provide a self-contained portable single patient ventilator/resuscitator of the type having a chemical oxygen generator, the ventilator/resuscitator further including an accumulator adapted to receive oxygen from the chemical oxygen generator durng exhalation, and also being adapted to supplement the oxygen provided by the chemical oxygen generator during inhalation, such a ventilator/resuscitator having an extended shelf life and a satisfactory operational duty cycle.

It is a further object of the present invention to provide a self-contained portable single patient ventilator/resuscitator of the type set forth above wherein the ventilator/resuscitator is provided with a suction pump and a filter, the unit being capable of entraining filtered air into the output of the oxygen generator to further extend its operational duty time.

The foregoing objects and other objects and advantages of this invention will become more apparent from a consideration of the following detailed description taken in conjunction with the accompanying figure.

BRIEF DESCRIPTION OF THE DRAWINGS

FIG. 2 is a simulated pressure-time curve showing a normal inspiratory/exhalation cycle and also patient triggered inspiratory and exhalation cycles wherein the patient has bypassed the normal cycle to satisfy his physiological needs.

DESCRIPTION OF A PREFERRED EMBODIMENT

Figure 1:
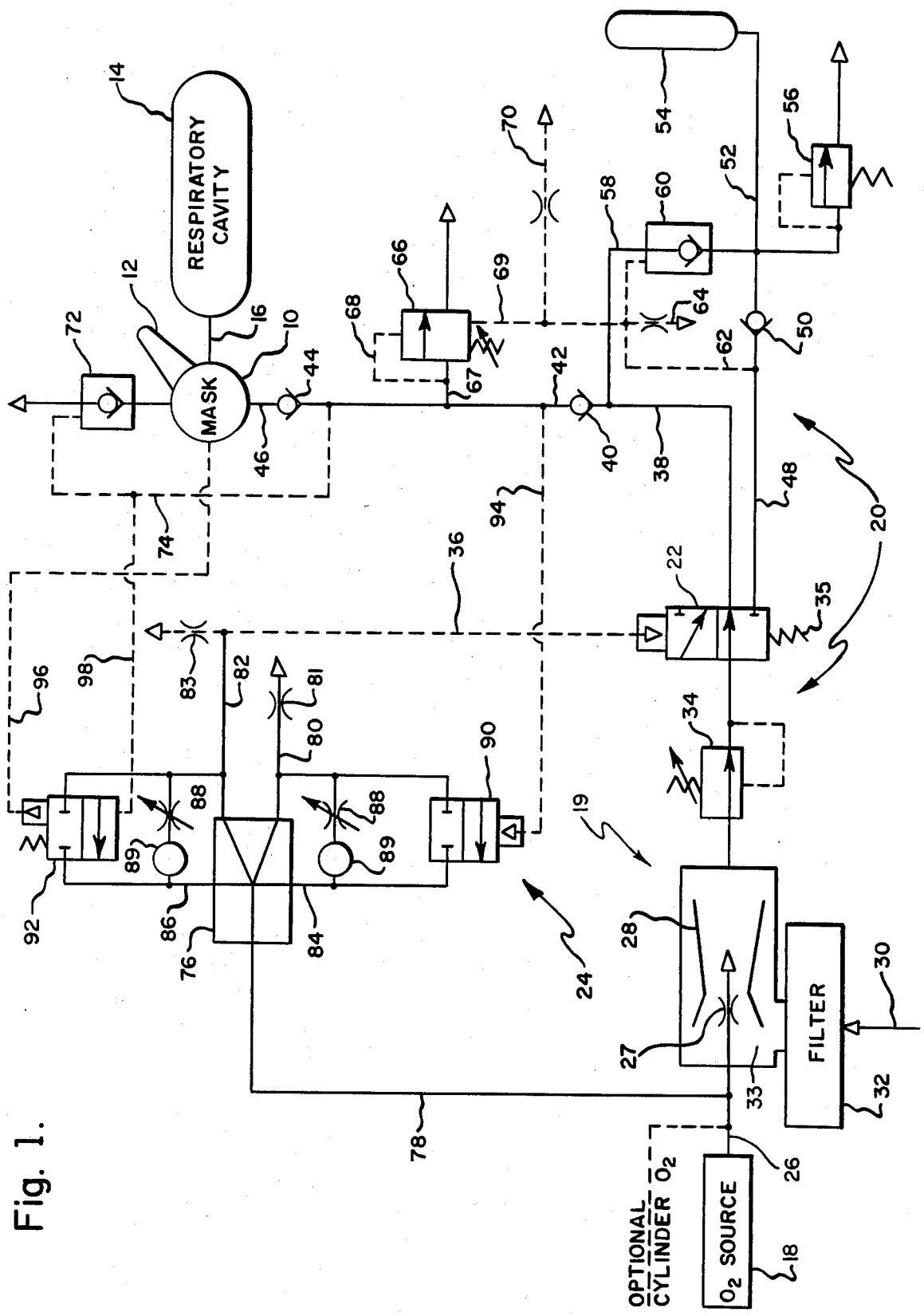
FIG. 1 is a somewhat schematic fluid circuit diagram illustrating the principles of the present invention.

Referring now to FIG. 1, a self-contained portable single patient ventilator/resuscitator is shown in a system diagram. The ventilator/resuscitator includes a mask 10 which is adapted to be secured to a patient through head harness means 12, the patient in part being indicated by the respiratory cavity 14 and the patient's air passages 16. The ventilator/resuscitator further includes power supply means including a source of oxygen in the form of a chemical oxygen generator 18, delivery means indicated generally at 20 and fluid operated control means indicated generally at 24. The delivery means includes, in addition to the mask 10 and head harness 12, two position flow directing means in the form of a valve 22 which is shiftable between inspiratory and expiratory positions, suction pump means indicated generally at 19, and other fluid components disposed between the source of oxygen 18 and the mask 10.

The chemical oxygen generator is preferably a chlorate candle. Chlorate candles are well known in the art and one such candle is disclosed in U.S. Pat. No. 2,507,450. The chlorate candle, when in operation, discharges oxygen through outlet means 26 which also forms part of the power supply means.

The suction pump means 19 includes a jet orifice 27, the output of the chlorate candle being directed through the jet orifice 27 and then through a venturi 28. In accordance with well-known principles, as the velocity of the oxygen.increases, its pressure will drop. This drop in pressure is utilized to introduce ambient air, indicated by arrow 30, into the system, the air passing through an activated charcoal filter or the like, indicated at 32, and then through the inlet or suction portion 33 of the suction pump means. The purpose of the filter is to remove toxic or harmful contaminants from the ambient air. The filter has a filter inlet open to ambient air and a filter outlet connected to the suction portion 33 of the suction pump means 19. The filter ambient air will be mixed with the oxygen downstream of the jet orifice 27, and the filtered air and oxygen will be discharged through the discharge portion of the pump means 19. A pressure or flow regulating valve indicated at 34 is disposed downstream of the pump means for insuring that a relatively constant output is provided to the valve 22.

The distributor valve 22 is basically a two position three port directional control valve which is normally held in the inspiratory position illustrated in the figure by the action of a spring 35, but which is shiftable to an expiratory position under the influence of pilot line pressure in pilot line 36. When the valve is in the inspiratory position illustrated in FIG. 1 the flow from the oxygen generator will be through the valve 22, line 38, check valve 40, outlet line 42, check valve 44, and line 46 into the mask 10 and then through the patient's air passage 16 into the respiratory cavity 14. This flow will continue until the valve 22 is shifted to its expiratory position by the influence of pilot line 36. When the valve 22 is in its expiratory position flow from the source of oxygen 18 will be through the valve 22 to accumulator means which includes line 48, check valve 50, line 52 and accumulator 54. If the pressure in accumulator 54 should exceed its design level, the additional pressure may be vented to atmosphere through pressure relief valve 56. The line 52 is connected with line 38 by a further line 58 provided with a compensated check valve 60. The valve 60 is compensated by means of a pilot line 62 which has associated therewith a bleed to atmosphere 64. Other fluid components in the oxygen delivery system are the positive end expiratory pressure (PEEP) valve which is in the form of a pressure compensated relief valve 66 which is connected to line 42 through line 67 and pilot line 68 and line 58 through pilot line 69 which is also provided with a bleed to atmosphere line 70. Finally, a compensated exhalation valve in the form of a pressure compensated check valve 72 is provided. The valve 72 is compensated by the pilot line 74 which extends from line 42. Typically, the check valve 44 and pressure compensated check valve 72 form a compensated inhalation/exhalation valve mounted on mask 10 at the end of the outlet line 42.

The control means 24 as illustrated is pneumatically operated and includes a fluidic flip-flop 76 whose input is connected with the source of oxygen through line 78. One such suitable flip-flop is the Norgren module 4FF-202.000. The output of the flip-flop can be through either line 80 or line 82, both of which are bled to atmosphere through restrictors 81 and 83, respectively. However, it should be noted that pilot line 36 extends from line 82 to control valve 22, the pilot line 36 being connected upstream of the restrictor 83. Input control lines 84 and 86 are also provided for the flip-flop. As is well known in the art, when the bistable flip-flop is subjected to pressure in control line 84 its output will be diverted from line 80 to line 82. Similarly, when the flip-flop 76 is subjected to pressure in line 86 its output will be diverted from line 82 to line 80. Each of these lines 84 and 86 are connected with an associated output line 80 or 82, respectively, by suitable valving. One such valve may be a timing module 88 and 89, and fluidic timing modules are well known in the art, one being the Norgren time delay module 5TD-214-000 which combines a fluidic resistance capacitance network with a Schmitt trigger, the module being provided with variable restrictor inputs. A fluidic timing module operates essentially by having a flow of control fluid pass through a variable orifice until certain predetermined volume has entered the module, at which point an output flow is then triggered. Thus, the adjustable orifice 88 disposed between lines 80 and 84 may be adjusted to cause the output flow to be triggered after two seconds. Similarly, the adjustable orifice 88 associated with lines 82 and 86 can be adjusted to cause the output flow to be triggered after four seconds. By utilizing such timing modules the operation of the control valve 22 can be controlled. However, as has been previously noted the patient's physiological needs may differ from the preset times established by the timing modules. Accordingly, additional controls are provided. One such control would normally block flow from line 80 to line 84 but would open when the pressure exceeded a predetermined limit, this control being indicated at 90. This control 90 will permit the timing module to be overridden under certain situations which are described below. Additional controls may be provided between line 82 and line 86, one such control 92 being opened when the pressure in the mask drops below that value established by valve 66, which would happen when the patient initiates an inhalation effort.

Pilot operated two position two port directional control valves are illustrated. Valve 90 is normally spring biased to a closed position, but will open when the pressure in pilot line 94 exceeds the value determined by the adjustable spring. Valve 92 is normally spring biased to a closed position, but when the patient initiates an inspiratory effort the pressure in the mask will drop below that determined by the PEEP valve, and these conditions will be sensed by pilot lines 96 and 98 causing the valve 92 to shift to its open position. While two position directional control devices are illustrated, it should be obvious that other control devices may be used, as for example, monostable flip-flops associated with suitable pressure relief valves. In addition, air logic control systems may be substituted for the various controls 76, 88, 89, 90 and 92.

In operation, let us assume that the operation of the chlorate candle 18 has just been initiated and that the output of the fluidic module is in line 80. The distributor valve 22 will be biased to the position illustrated in the drawing by the spring 35. Flow from the generator 18 will be through the suction pump 19 where it picks up air 30 which has passed through filter 32. The pressure of the output of the suction pump means 19 is regulated by regulating valve 34. In FIG. 2 the peak regulated pressure is illustrated at 25 cm H$_2$O. However, higher pressures may be desirable. Flow from valve 34 passes through valve 22 into line 38, check valve 40, and on to the mask 10 and into the patient 14. This flow will continue until either the timing module between lines 80 and 84 times out, or until the control 90 is shifted to permit flow from line 80 to 84. The pressure to which valve 90 responds can be adjusted as indicated in FIG. 1, but it would normally respond in one of two situations, namely when the patient is trying to exhale or when the patient's respiratory cavity has been filled to the set pressure. In either event the flow of oxygen and air through line 38 and check valve 40 has nowhere to go except to build up pressure in the pilot line 94 which extends between line 42 and control 90 causing the control to permit the flow of fluid from 80 to line 84 thereby shifting the output of the fluidic flip-flop 76 to line 82. After this event occurs several things happen. First, the valve 22 is shifted by the pressure in line 36 from the indicated position to that position where the output of the source of oxygen 18 is passed from valve 22 into line 48 and then into the accumulator 54. It should be noted at this point that the output of the chlorate candle is substantially constant over a given period of time and if it is not being used by the patient it must either be stored or be wasted. The accumulator provides a means whereby the output of the candle may be stored for subsequent use by the patient. When the valve is in the expiratory position the output of the candle will, in normal operation, go merely into the accumulator. Check valve 60 will not permit the accumulator to discharge its accumulated oxygen and air when line 48 is pressurized as the valve 60 is compensated by line 62. At the same time excess pressure in pilot line 62 will be bled to atmosphere through bleed 64. Similarly, excess pressure in lines 38, 58, and pilot line 69 are bled to atmosphere through bleed 70. This permits the pressure compensated relief valve or PEEP valve 66 to lower the pressure in pilot line 74 which compensates the exhalation valve 72. Meanwhile the patient will expire air through valve 72 until the PEEP pressure is obtained, which pressure is determined by the adjustable PEEP valve 66, and which may vary the pressure setting between 0 and 20 centimeters of water. When this pressure is attained, additional air will not be exhausted through valve 72. Customarily, exhalation occurs rapidly (within one second), and the remaining exhalation time (for example 3 seconds) is just a pause until inhalation occurs. Inhalation may be initiated by the timing module 88, 89, which is disposed between lines 82 and 86, having timed out causing fluid to be introduced into line 86 shifting the output of the fluidic module to line 80 thus ending the expiratory cycle. Alternatively, if the patient should attempt to inhale this would also cause the control 92 to open. Thus, when the pressure in pilot line 96 drops below the pressure in pilot line 98 which would happen when the patient attempts to inhale, the valve 92 will be shifted to its open position. When the output is again cycled back to line 80 the valve 22 will be shifted to the position indicated in FIG. 1. Additional oxygen and air will now flow into the mask from the pump means 28 and also from the accumulator which will unseat the check valve 60 as it is no longer being compensated through line 62, this line having bled out through bleed 64. The pressure in line 38, 58, and 69 will also cause the PEEP valve to be biased to a closed position preventing fluid from being exhausted through this valve. By allowing the patient's natural physiological needs to sequence the inspiratory/expiratory cycle it will permit the attending person to address other needs. Prior art portable and/or pneumatically controlled ventilator/resuscitators will not allow a timed inspiratory/expiratory cycle to lengthen or shorten automatically as needed but must be adjusted manually to match the needs of the patient.

It should be noted that one of the advantages of the device described above is that the control means is operated solely by the output of the oxygen source. It has been found in practice that chlorate candles have an extremely long and reliable shelf life, for example 10 years or more. Thus, by using its output to control the cycling of the unit as well as its pressure compensation, a highly reliable ventilator/resuscitator is provided which additionally has a long shelf life.

What is claimed is:

1. A self-contained portable single patient ventilator/resuscitator capable of operating without attention for a period of time after its operation has commenced; said ventilator/resuscitator comprising:

power supply means capable of discharging oxygen over a period of time at a pressure sufficiently great to force oxygen into a patient's lungs, said power supply means including a chemical oxygen generator and outlet means;

delivery means extending from said outlet means and capable of causing at least a portion of said oxygen to be delivered from said outlet means to said patient, said delivery means including
a mask,
head harness means connected to said mask and capable of holding said mask onto said patient,
suction pump means capable of being operated when receiving oxygen from the outlet means of said power supply means to cause ambient air to be drawn into said pump means, to be mixed with said oxygen within said pump means, and to be discharged from said pump means, said suction pump means including a jet orifice interconnected to said outlet means and which receives oxygen from said power supply means, a suction portion which receives ambient air during operation of said power supply means, and a discharge portion through which mixed oxygen and ambient air are discharged during operation of said power supply means,
two position flow directing means capable of being shifted between inspiratory and expiratory positions, and
fluid line means interconnected with the two position flow directing means and capable of delivering mixed oxygen and ambient air from the discharge portion of the suction pump means to said mask when the two position flow directing means is in its inspiratory position;

fluid operated control means operated by the oxygen discharged by said power supply means and capable of causing said two position flow directing means to be shifted between inspiratory and expiratory positions and to be maintained in each of said positions for first and second limited time periods, a portion of said oxygen being delivered to said mask when the two position flow directing means is in said inspiratory position;

further fluid line means interconnecting said fluid operated control means with the outlet means of said power supply means and said two position flow directing means; and wherein said delivery means further includes accumulator means interconnected with the two position flow directing means, said accumulator means and the two position flow directing means being capable of causing at least a portion of the oxygen discharged by the power supply means to be delivered to the accumulator means when the two position flow directing means is in its expiratory position and also being capable of causing the accumulated oxygen to be delivered to a patient when the two position flow directing means is in its inspiratory position.

2. The self-contained portable single patient ventilator/resuscitator as set forth in claim 1 further comprising filter means capable of filtering out toxic and harmful contaminants from ambient air, said filter means including a filter inlet open to ambient air and a filter outlet, the filter outlet being interconnected to the suction portion of the suction pump means.

3. The self-contained portable single patient ventilator/resuscitator as set forth in claim 1 further comprising filter means capable of filtering out toxic and harmful contaminants from ambient air, said filter means including a filter inlet open to ambient air and a filter outlet, the filter outlet being interconnected to the suction portion of the suction pump means.

4. The self-contained portable ventilator/resuscitator as set forth in one of claims 1, 2 or 3 wherein said oxygen generator is a chlorate candle.

5. The self-contained portable ventilator/resuscitator as set forth in one of claims 1, 2 or 3 wherein the fluid operated control means further includes pressure sensing control means capable of causing said delivery means to shift between the inspiratory and expiratory modes prior to the expiration of the associated limited timed period and in response to changes of pressure in the delivery means.

6. The self-contained portable ventilator/resuscitator as set forth in claim 5 wherein said delivery means is caused to be shifted to its inspiratory mode by said pressure sensing control means when the patient initiates an inspiratory effort, and wherein said delivery means is caused to be shifted to its expiratory mode by said pressure sensing control means when the pressure to the patient exceeds a set peek pressure.

7. The self-contained portable ventilator/resuscitator as set forth in claim 6 wherein the oxygen generator is a chlorate candle.

8. A self-contained portable single patient ventilator/resuscitator capable of operating without attention for a period of time after its operation has commenced; said ventilator/resuscitator comprising:
  power supply means capable of discharging oxygen over a period of time at a pressure sufficiently great to force oxygen into a patient's lungs, said power supply means including a chemical oxygen generator and outlet means;
  filter means capable of filtering out toxic and harmful contaminants from the ambient air, said filter means including a filter inlet open to ambient air and a filter outlet.
  delivery means extending from said outlet means and capable of causing at least a portion of said oxygen to be delivered from said outlet means to said patient, said delivery means including
    a mask,
    head harness means connected to said mask and capable of holding said mask onto said patient,
    suction pump means capable of being operated when receiving oxygen from the outlet means of said power supply means to cause ambient air to be drawn into said pump means, to be mixed with said oxygen within said pump means, and to be discharged from said pump means, said suction pump means including a jet orifice interconnected to said outlet means and which received oxygen from said power supply means, a suction portion capable of receiving ambient air during operation of said pump means, and a discharge portion through which mixed ambient air and oxygen are discharged during operation of said pump means, said suction portion being connected to the filter outlet, and said jet orifice being connected to the outlet means of said power supply means,
    two position flow directing means capable of being shifted between inspiratory and expiratory positions,
    accumulator means interconnected with the two position flow directing means, said accumulator means and the two position flow directing means being capable of causing at least a portion of the oxygen discharged by the power supply means to be delivered to the accumulator means when the two position flow directing means is in its expiratory position and also being capable of causing the accumulated oxygen to be delivered to a patent when the two position flow directing means is in its inspiratory position, and
    fluid line means interconnected with the two position flow directing means and capable of delivering mixed oxygen and ambient air from the discharge portion of the suction pump means to said mask when the two position flow directing means is in its inspiratory position;
  fluid operated control means operated by the oxygen discharged by said power supply means and capable of causing said two position flow directing means to be shifted between inspiratory and expiratory positions and to be maintained in each of said positions for first and second limited time periods, a portion of said oxygen being delivered to said mask when the two position flow directing means is in said inspiratory position; and
  further fluid line means interconnecting said fluid operated control means with the outlet means of said power supply means and said two position flow directing means.

9. The self-contained portable single patient ventilator/resuscitator as set forth in claim 8 wherein the chemical oxygen generator is a chlorate chandle.

10. The self-contained portable single patient ventilator/resuscitator as set forth in claim 8 wherein the control means includes pressure sensing control means capable of causing said two position flow directing means to be shifted to its first position when a patient initiates an inspiratory effort and to shift said flow directing means to its second position, when the pressure to the patient exceeds a set pressure.

11. The self-contained portable single patient ventilator/resuscitator as set forth in claim 10 wherein said pressure sensing control means includes two shiftable valves, one valve being shifted during an exhalation effort by the patient and the other valve being shifted during an inhalation effort.

12. A self-contained portable single patient ventilator/resuscitator capable of operating without attention for a period of time after its operation has commenced; said ventilator/resuscitator comprising:
  power supply means capable of discharging oxygen over a period of time at a pressure sufficiently great to force oxygen into a patient's lungs, said power supply means including a chemical oxygen generator and outlet means;
  filter means capable of filtering out toxic and harmful contaminants from ambient air, said filter means including a filter inlet open to ambient air and a filter outlet;
  delivery means extending from said outlet means and capable of causing at least a portion of said oxygen to be delivered from said outlet means to said patient, said delivery means including
    a mask, head harness mean connected to said mask and capable of holding said mask onto said patient, suction pump means capable of being operated when receiving oxygen from the outlet means of said power supply means to cause ambient air to be drawn into said pump means, to be mixed with said oxygen within said pump means, and to be discharged from said pump means, said suction pump means including a jet orifice which received oxygen from said power supply means, a suction portion capable of receiving ambient air during operation of said pump means, and a discharge portion through which mixed ambient air and oxygen are discharged during operation of said pump means, said suction portion being connected to the filter outlet, and said jet orifice being connected to the outlet means of said power supply means, two position flow directing means capable of being shifted between inspiratory and expiratory positions, said two position flow directing means being interconnected with the discharge portion of the suction pump means, accumulator means interconnected with the two position flow directing means, said accumulator means being capable of storing mixed ambient air and oxygen when the two position flow directing means is in its expiratory position and being capable of discharging the stored air and oxygen when the two position flow directing means is in its inspiratory position, and fluid line means extending between the two position flow directing means, the mask, and the accumulator means and capable of delivering mixed oxygen and ambient air from the two position flow directing means and said accumulator means to said mask when the two position flow directing means is in its inspiratory position and also being capable of delivering mixed oxygen and ambient air from the two position flow directing means to the accumulator means when the two position flow directing means is in its expiratory position;

fluid operated control means operated by the oxygen discharged by said power supply means and capable of causing said two position flow directing means to be shifted between inspiratory and expiratory positions and to be maintained in each of said positions for first and second limited time periods, a portion of said oxygen being delivered to said mask when the two position flow directing means is in said inspiratory position; and further fluid line means interconnecting said fluid operated control means with the outlet means of said power supply means and said two position flow directing means.

* * * * *